US007581367B2

(12) United States Patent
Bechini

(10) Patent No.: US 7,581,367 B2
(45) Date of Patent: Sep. 1, 2009

(54) COMPACT SYSTEM FOR PACKAGING INJECTABLE LIQUID PRODUCTS INTO CONTAINERS IN A STERILE ENVIRONMENT

(75) Inventor: Claudio Bechini, Castelnuovo Berardenga (IT)

(73) Assignee: IMA Industria Macchine Automatiche S.p.A., Ozzano dell'Emilia (IT)

( * ) Notice: Subject to any disclaimer, the term of this patent is extended or adjusted under 35 U.S.C. 154(b) by 0 days.

(21) Appl. No.: 11/795,133

(22) PCT Filed: Jan. 11, 2006

(86) PCT No.: PCT/EP2006/000167

§ 371 (c)(1), (2), (4) Date: Jul. 12, 2007

(87) PCT Pub. No.: WO2006/074904

PCT Pub. Date: Jul. 20, 2006

(65) Prior Publication Data

US 2008/0141622 A1 Jun. 19, 2008

(30) Foreign Application Priority Data

Jan. 12, 2005 (IT) ....................... B02005A000010

(51) Int. Cl.
*B65B 55/02* (2006.01)
*A61L 2/00* (2006.01)

(52) U.S. Cl. ......................... 53/111 R; 53/425; 53/431; 422/292; 422/304

(58) Field of Classification Search ................... 53/425, 53/432, 431, 512, 111 R; 422/292, 294, 422/299, 304
See application file for complete search history.

(56) References Cited

U.S. PATENT DOCUMENTS 599,205 A * 2/1898 Vause .......................... 53/281

(Continued)

FOREIGN PATENT DOCUMENTS

DE 20 2004 001 619 U1 5/2004

OTHER PUBLICATIONS

International Search Report for PCT/EP2006/000167 mailed Jun. 28, 2006.

*Primary Examiner*—Paul R Durand
(74) *Attorney, Agent, or Firm*—Nixon & Vanderhye P.C.

(57) ABSTRACT

A compact system for packaging sterile pharmaceutical liquid products injectable into suitable containers in a sterile environment comprises a plurality of operative packaging stations connected together and arranged in succession along an advancing path of said containers; the plurality of stations comprises at least a washing station intended for cleaning and decontaminating each of the said containers, at least a sterilizing station for sterilizing the containers exiting said washing station, and at least a filling and sealing station for filling said containers with said liquids and for sealing said containers; said stations and a connecting arrangement thereof are mounted in an operating configuration on a sole work platform; the washing station and the sterilizing station being arranged parallel and alongside one another, and connected together by a first conveyor of the containers arranged transversely to the washing station and to the sterilizing station to define a first substantially "U"-shaped portion of said path; the filling and sealing station being arranged aligned on said washing station and connected, in a staggered position, to the sterilizing station by a second conveyor of said containers arranged transversely to the sterilizing station, to define a second substantially "L"-shaped portion of the advancing path.

17 Claims, 4 Drawing Sheets

Figure 1:
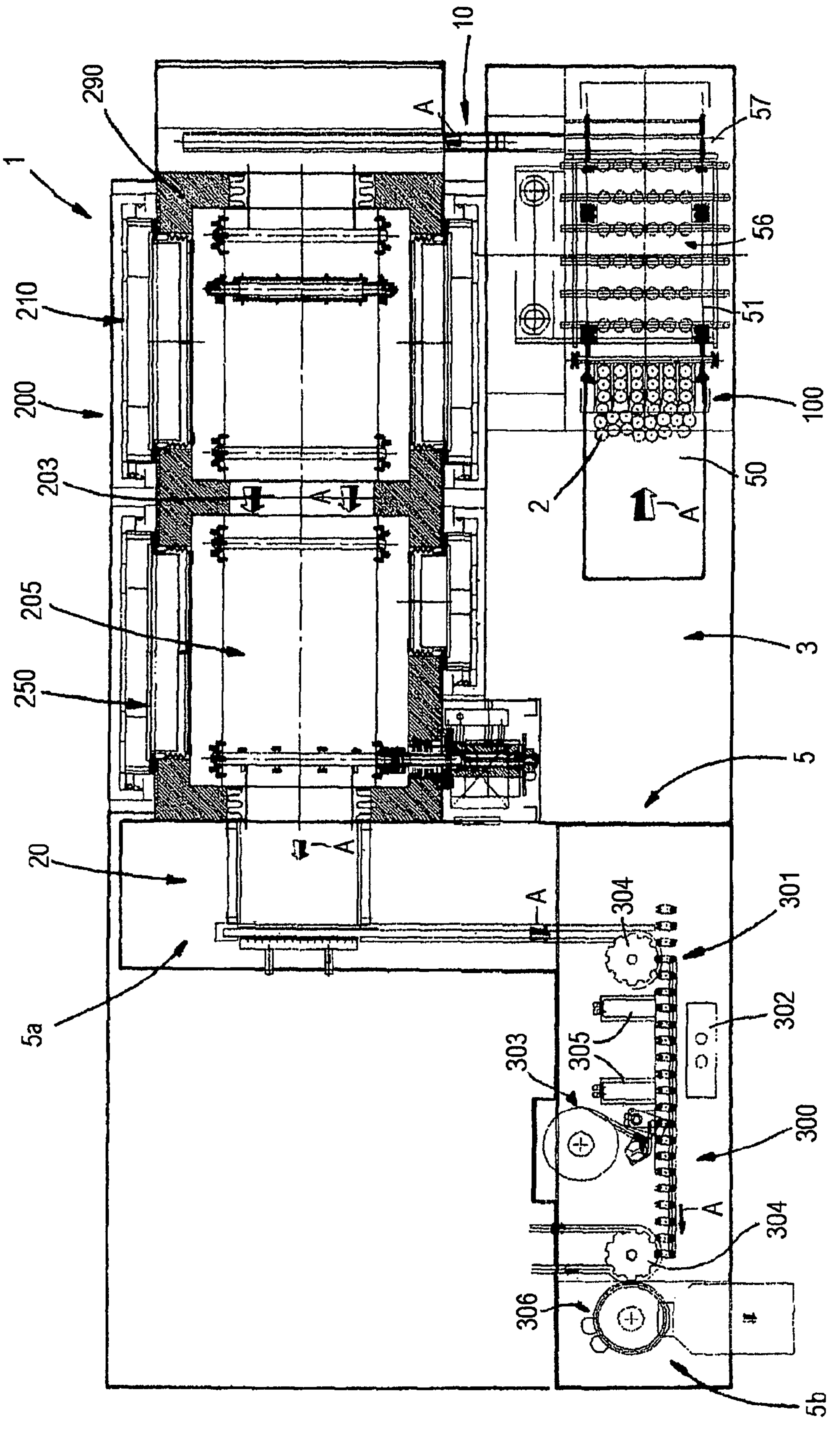

U.S. PATENT DOCUMENTS 3,747,296 A * 7/1973 Zausner ........................ 53/167
4,296,068 A * 10/1981 Hoshino ....................... 422/62
4,533,515 A * 8/1985 Witter et al. .................. 422/26
4,707,334 A * 11/1987 Gerhard ....................... 422/28
4,862,933 A * 9/1989 Gies ........................... 141/130
4,979,347 A * 12/1990 Shibauchi et al. ............. 53/167
5,129,212 A * 7/1992 Duffey et al. ................. 53/426
5,135,014 A 8/1992 Beswick
5,178,841 A * 1/1993 Vokins et al. ............... 422/298
5,258,162 A * 11/1993 Andersson et al. ............ 422/28
5,368,828 A * 11/1994 Carlson ...................... 422/300
5,377,475 A * 1/1995 Haarer et al. ................. 53/167
5,896,899 A 4/1999 Schmitz
6,039,922 A * 3/2000 Swank et al. .................. 422/24
6,120,730 A * 9/2000 Palaniappan et al. .......... 422/28
6,185,910 B1 * 2/2001 Achhammer ................. 53/426
6,436,343 B1 * 8/2002 Bechini ....................... 422/28
6,475,435 B1 * 11/2002 Taggart ....................... 422/23
7,357,159 B2 * 4/2008 Popplau ....................... 141/92
2001/0029999 A1 10/2001 Reinecke

* cited by examiner

COMPACT SYSTEM FOR PACKAGING INJECTABLE LIQUID PRODUCTS INTO CONTAINERS IN A STERILE ENVIRONMENT

This application is the US national phase of international application PCT/EP2006/000167 filed 11 Jan. 2006 which designated the U.S. and claims benefit of IT BO2005A000010, dated 12 Jan. 2005, the entire content of which is hereby incorporated by reference.

The present invention forming a part of the technical field relating to the packaging of pharmaceutical products in a protected environment.

In particular, the invention refers to a complete and compact system for sterile packaging with integrated washing, sterilising/depyrogenating and subsequent filling of containers with liquids, in particular injectable liquids for use in thebiotechnological field, to which the following disclosure will refer explicitly without thereby losing in generality. Specifically, the packaging system in object operates in a zone provided with an insulating arrangement suitable for preventing contamination coming from outside and between different parts of the system, and for furthermore preventing contamination of the external environment by the system.

In general, packaging systems are known, each of which is defined by a plurality of operating machines connected together, such as example a washing operating machine for washing the containers that is connected to a sterilising tunnel machine for sterilising the containers that is connected to a filling machine for filling the containers with liquids, in turn connected to a capping/sealing machine for sealing the filled containers.

A packaging system of the aforementioned type generally provides for installing of auxiliary devices such as conveyors or sections of connector between consecutive operating machines and furthermore comprises micro filtrating apparatuses and laminar air-flow generating apparatuses in addition to structures suitable for isolating the system from the external environment.

Furthermore, in the same system connections are provided for supplying the liquid product to be packaged, the replacement air and any materials used for periodic sterilising of the system.

Currently, such a constructional set-up has the drawback of occupying very important productive spaces and with great overall dimensions, not only because of the significant dimensions of the various operating machines connected together but also because the respective connectors and connecting and conveying devices are often of significant dimensions, also because they have to adapt to the conformation of the various operating machines.

Furthermore, with a system that is structured in such a way and with such significant dimensions, the usual and complex validation tests, that are designed to test the suitability of the system for treating pharmaceutical products for which the system has been designed in compliance with all current legislation, need to be conducted several times.

In fact, an initial validation phase is conducted on the premises of the manufacturer where the machines forming part of the system were assembled together for an initial testing phase.

Once this first validation phase has been completed, the system then has to be disassembled and conveyed by blocks to the operating working premises of the system, where the system is reassembled.

Once reassembling has been carried out it is then necessary to repeat anew, in addition to the in situ testing operations, all the validation tests that are necessary in order to deliver to the end user a perfectly functioning system and which conforms to regulations.

As can be easily intuitable, this involves very great waste of resources in terms of use highly specialised technicians in addition to a generally very high installation cost.

Such significant drawbacks are particularly evident and felt above all in the pharmacological industry, and in particular in the field of so-called "biotechnology", where on the other hand the need has currently emerged to package large volumes of batches of product at reduced costs and for relatively limited periods.

In fact, these products are generally new drugs being clinically tested, or drugs intended for limited diffusion, and are packaged by companies that in most cases are structured as research laboratories. The dimension of the logistic structures is generally limited, whereas the number of products being tested/in production and the frequency of alternating thereof on the production lines are particularly high.

An object of the present invention is thus to provide a system for packaging in a sterile environment liquid products, in particular injectable liquids, in containers, which is free of the drawbacks of the prior art disclosed above.

In particular, an object of the present invention is to provide a packaging system structure for liquid products in a protected environment of compact type and which is able to meet all the productive needs set out above.

A further object of the invention is to provide a particularly efficient packaging system and which is able to optimise energy consumption on the production site.

According to the present invention a compact system is provided for packaging in a sterile environment liquid products, in particular injectable pharmaceutical liquids, into suitable containers, the system comprising a plurality of operative packaging stations connected together and arranged in succession along an advancing path of the said containers; said plurality of stations comprising at least a washing station intended for cleaning and decontaminating each of the said containers, at least a sterilising station for sterilising the containers exiting said washing station, and at least a filling and sealing station for filling said containers with said liquids and for sealing the containers; wherein said stations and a connecting arrangement thereof are mounted in an operating configuration on a sole work platform; said washing station and said sterilising station being arranged parallel to one another and placed alongside and connected together by a first conveyor of the containers arranged transversely to the washing station and the sterilising station to define a first substantially "U"-shaped portion of the said path; said filling and sealing station being arranged aligned on said washing station and connected, in a staggered position, to said sterilising station by a second conveyor of said containers arranged transversely to the sterilising station, to define a second substantially "L"-shaped portion of said advancing path.

Figure 2A:
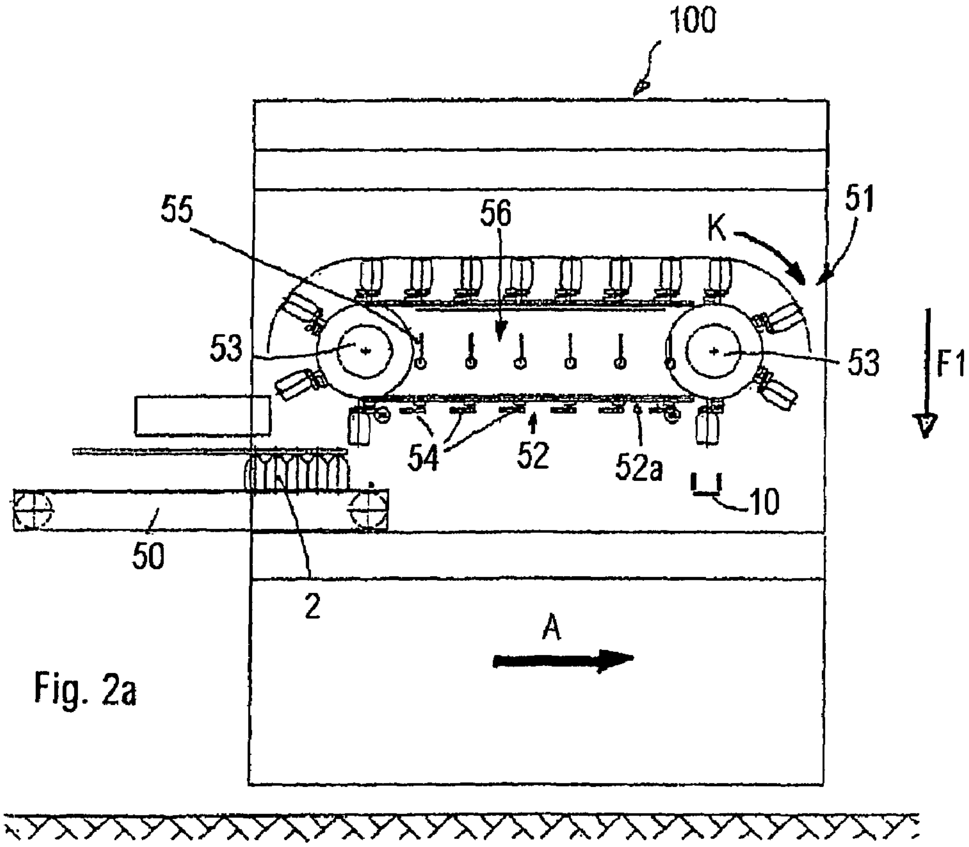
Figure 2B:
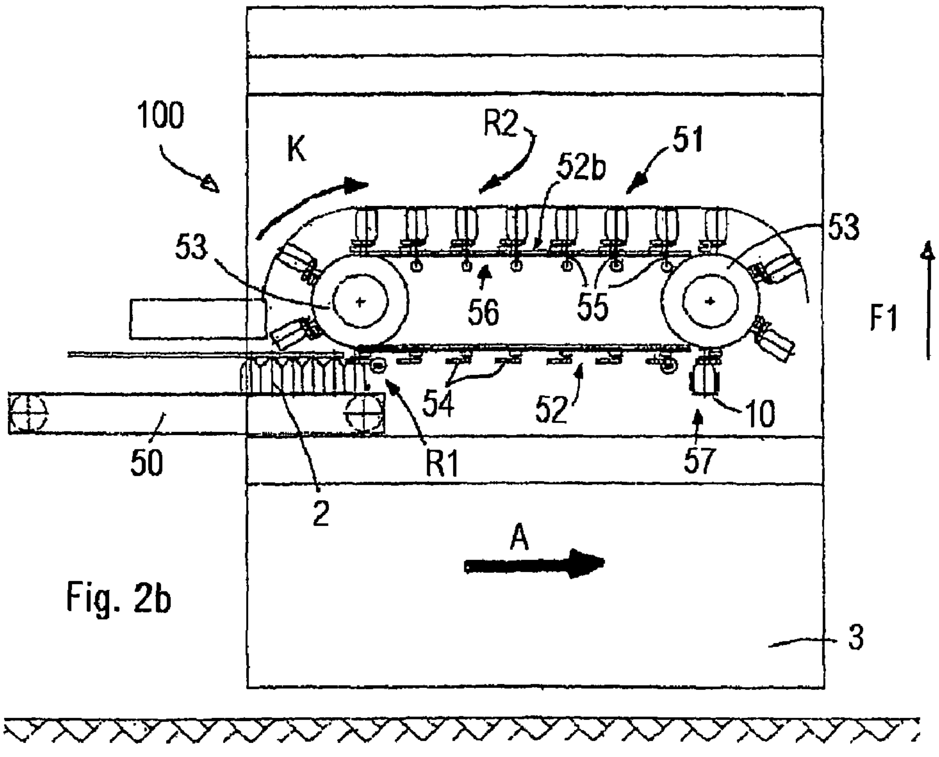
Figure 3:
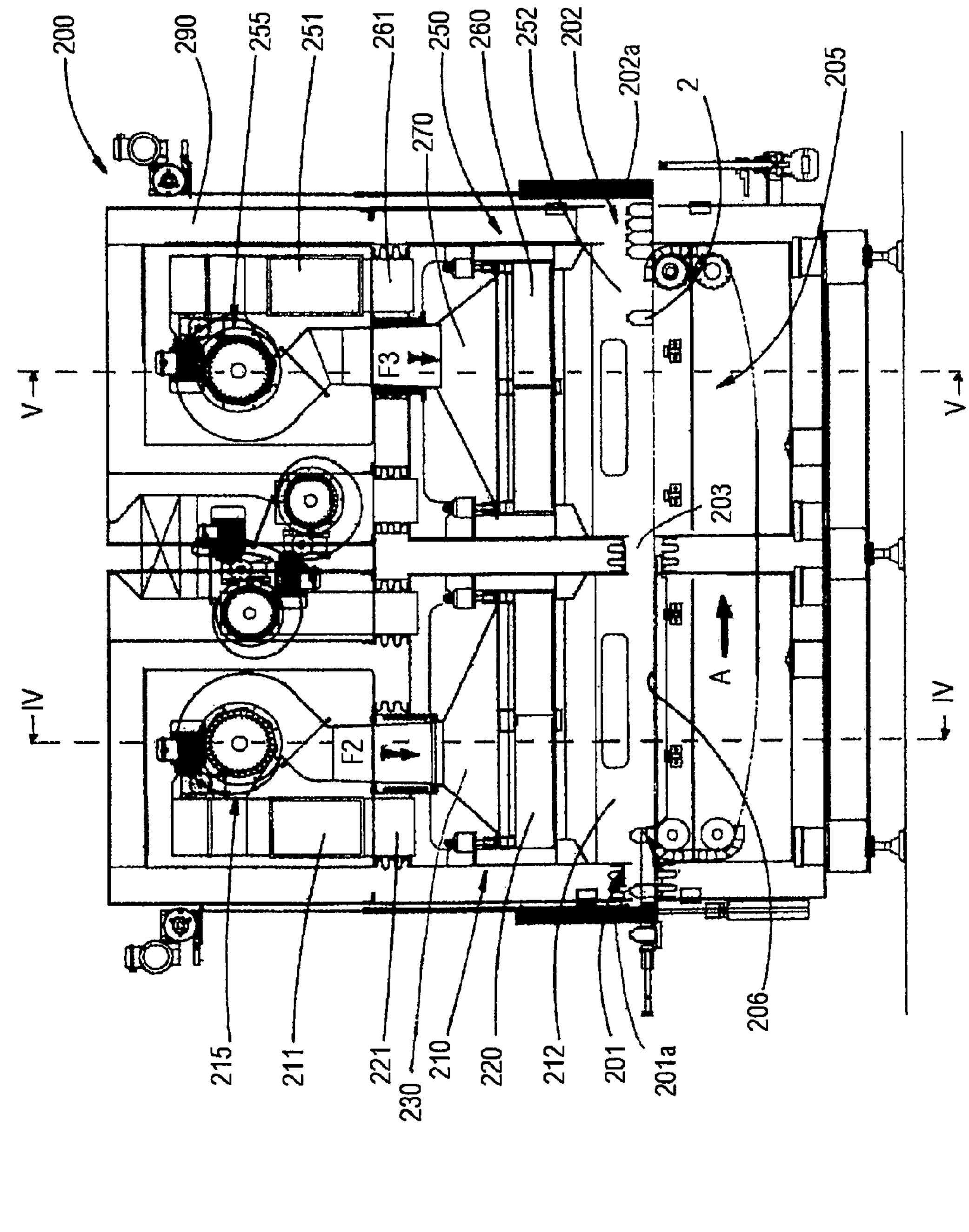
Figure 4:
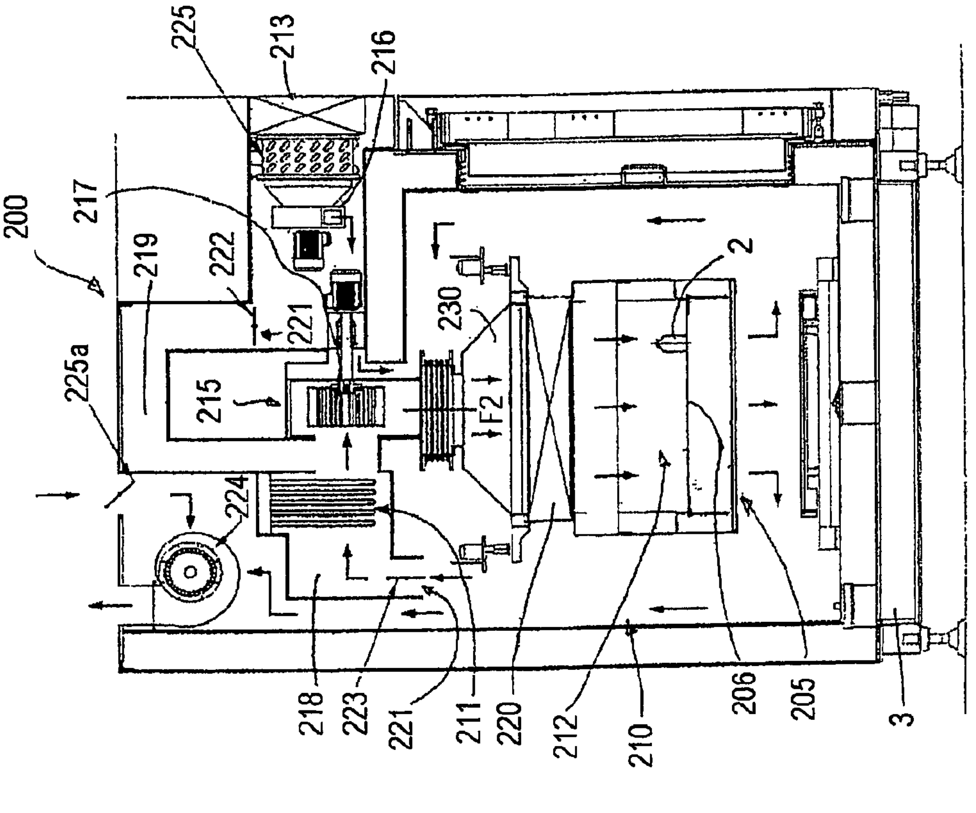
Figure 5:
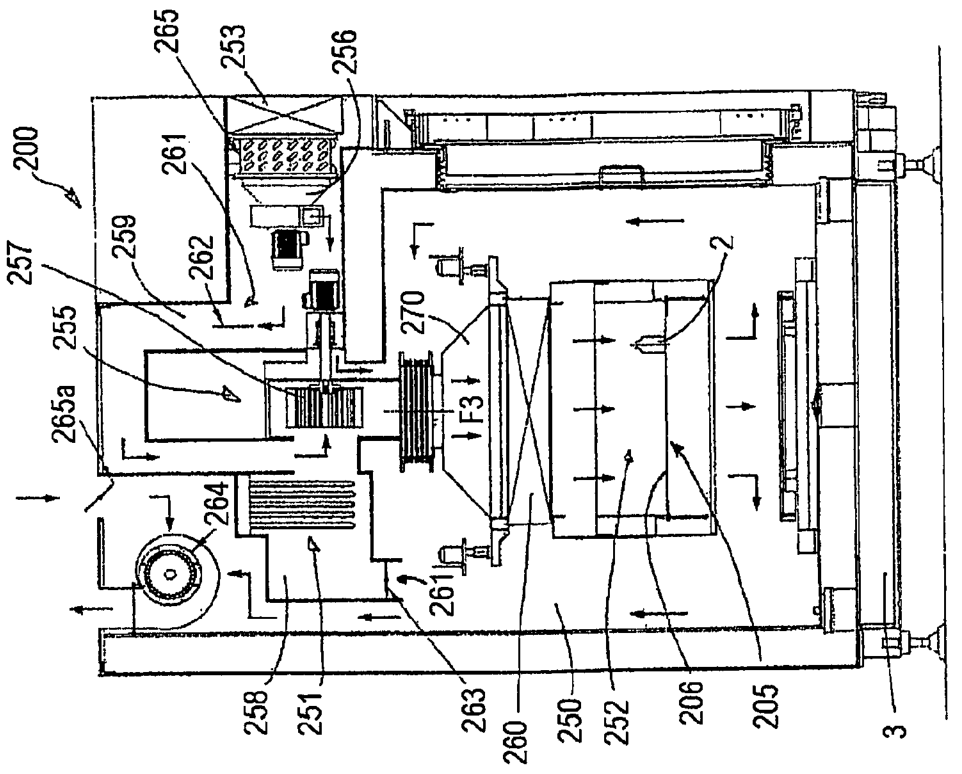

The technical features of the invention according to the aforementioned objects are clearly ascertainable by the contents of the claims set out below, and the advantages thereof will be clearer in the detailed disclosure that follows, with reference to the attached drawings, that show an embodiment thereof purely by way of non-limitative example, in which:

FIG. 1 illustrates schematically a partially sectioned plan view and with some parts removed for clarity, of an embodiment of a compact packaging system according to the present invention;

FIGS. 2*a*, 2*b* are schematic frontal and section views of an operating station of the system of FIG. 1 in two different respective functional positions;

FIG. 3 schematically illustrates a frontal and section view of another operating station of the packaging system of FIG. 1; and FIGS. 4 and 5 illustrate two respective section views according to IV-IV and respectively according to V-V of the same operating station of FIG. 3, illustrated in two respective different functional positions.

With reference to the attached FIG. 1, 1 indicates overall a compact and automatic system particularly designed for packaging, in a protected environment, liquid pharmaceutical products for use in the biotechnological field inside suitable containers 2 and similar, for example, vial, syringes or bottles 2, according to an embodiment of the invention.

The system 1 comprises a plurality of operating stations 100, 200 and 300 connected together and integrated and arranged consecutively in relation to an advancing conveying plane path A of the bottles 2 to be filled, according to a particular configuration, as will be disclosed in detail below.

In particular, all the operating stations 100, 200, 300 and corresponding, connecting members 10, 20 of the system 1 are mounted and arranged on a single platform 3 dimensioned in such a way as to occupy a rectangular area the same as the area of a loading plane of a standard road transport vehicle, so as to be compatible with the loading and conveying of the entire system 1 mounted on the plane, the system 1, thus all the aforementioned operating stations that compose the latter, is furthermore managed and controlled by a sole control unit (known and not illustrated).

In the embodiment illustrated in FIG. 1, the system 1 comprises a washing station 100 of empty bottles 2 intended for washing and decontaminating each empty bottle 2 of any organic or inorganic residue present inside the bottle 2 before filling with the liquid product.

The washing station 100 extends longitudinally on the platform 3, and has particularly compact dimensions.

According to what has been illustrated in FIGS. 2*a* and 2*b*, the washing station 100, that is specifically the object of a separate patent application filed together with the current application by the same applicant, comprises a conveying plane 50 suitable for defining the inlet of the entire system 1 and on which the empty bottles 2 are deposited to be supplied in an orderly manner along the path A with their open inlets facing upwards, to a conveyor 51 of the belt 52 type wound in a loop and moveable in step mode around a corresponding pulley 53 and supporting a plurality of grasping grippers 54.

According to what has been illustrated in FIG. 2*b*, during step movement of the belt 52 around the pulleys 53 (direction K in FIGS. 2*a* and 2*b*), at a lower operating position R1 the grippers 54 temporarily arranged on the lower branch 52*a* of the belt 52 are each suitable for grasping by the neck a corresponding bottle 2 from the plane 50 and advancing a corresponding group of bottles 2 until the bottles 2 of the group are turned 180° in relation to the position taken on the plane 50, namely with their open inlet facing downwards.

In this configuration (upper branch 52*b* of the belt 52), the entire conveyor 51 is suitable for moving by means of a known moving arrangement and which is not illustrated and for example applied to the aforementioned pulleys 53, vertically downwards (arrows F1 in FIGS. 2*a* and 2*b*) reaching a second operating position R2 in which each nozzle 55 of a bank 56 of washing nozzles 55 is suitable for being inserted through the open inlet inside a corresponding bottle 2 overturned in such a way as to be able to spray the inside of the bottle 2 with a sterilising washing liquid.

As can be observed in FIG. 2*b*, owing to the structure of the conveyor 51 that is movable with reciprocating motion in a vertical direction, the removing and grasping position R1 of a first group of bottles 2 from the plane 50, and the inserting position R2 of the nozzles 55 into the bottles 2 of a subsequent group of bottles 2 arranged on the upper branch 52*b* and therefore with the washing of the bottles 2 of the this subsequent group, are achieved simultaneously with great simplification of movements and overall dimensions. In other words, during use, the grasping of the aforementioned first group of bottles 2 from the plane 50 by means of the grippers 54 supported by the belt 52 in the position R1 is achieved during inserting of the nozzles 55 inside the bottles 2 of the subsequent group at the operating position R2.

Lastly, the station 100 comprises an outlet 57, at which the washed bottles 2 are unloaded from the conveyor 51 with grippers 54 to be deposited on a connecting conveyor 10 arranged transversely to the plane 50.

In a version that is not illustrated, the conveyor 51 is provided fixed in relation to the bank 56 of nozzles 55, whilst the latter are fitted movable with reciprocating motion from and to the bottles 2 to be inserted inside the bottles 2 and to achieve the washing thereof.

According to what has been illustrated in FIG. 1 and in FIG. 3, the system 1 furthermore comprises a sterilising station 200, defined by a two-stage sterilising unit 200, which is also arranged longitudinally on the platform 3 intended for receiving the bottles 2 exiting the station 100 and advanced by the conveyor 10 to carry out the sterilising/depyrogenating of the bottles 2.

Still according to what has been illustrated in FIG. 1, the station 200 extends substantially parallel to the washing station 100 and is conveniently arranged in a position laterally alongside the washing station 100, such that the advancing directions of the bottles 2 along a "U" section of the path A at the two stations 100 and 200 alongside one another are opposite one another.

The sterilising unit 200, that is the specific subject of a separate patent application filed at the same time as this application by the same applicant, comprises in an embodiment illustrated in FIGS. 1 and 3, a pair of sterilising modules, respectively a first module 210 and a second module 250, arranged consecutively and communicating together by means of an intermediate passage 203.

These modules 210 and 250 of the station 200 are activatable independently of one another according to hot and/or cold sterilising modes of the bottles 2.

In other words, by suitably activating in relation to one another the modules 210 and 250, as will be explained better below, it is possible to achieve excellent sterilisation of the bottles 2 with the following four alternative operating modes: hot-cold, hot-hot, cold-cold, or, lastly, cold-hot.

The entire unit 200 is enclosed within an insulated covering structure 290 intended for preventing significant heat loss to the external environment.

The unit 200 furthermore provides a belt conveyor 205, arranged at the bottom part thereof between a loading inlet 201, made in the first sterilising module 210, and an unloading outlet 202, made in the second sterilising module 250.

According to what has been illustrated in FIGS. 1 and 3, the conveyor 205 is intended for supporting the bottles 2 on an upper branch 206 thereof to convey the bottles 2 inside and through the first and second module 210 and 250 according to sequences that will be more fully detailed below.

The loading inlet 201 and the unloading outlet 202 are provided with corresponding gate valves 201*a*, 202*a* (FIG. 3), suitable for enabling the opening and closing thereof for the respectively passage of the entering and exiting bottles 2.

In the first sterilising module 210 a sterilising chamber 212 is obtained, the lower part of which is crossed by the aforementioned conveyor 205.

As better illustrated in FIG. 3, in the upper part of the first module 210 by means of suitable conduits and separating baffles an air flow F2 is created that is intended for being blown towards the bottles 2 according to the modes disclosed below to define two different heating or cooling paths of the alternately selectable bottles 2.

This flow F2 flows, above the conveyor 205, into a bell 230, below which a filtering element 220 is provided, defined for example by a HEPA filter of suitable class for obtaining the desired degree of air purity.

In the first module 210 a generating device 215 of the aforementioned air flow F2 is also provided.

The first 210 and second 250 sterilising modules can have a substantially identical structure: thus, similarly to the first module 210, also the second module 250 is suitable for defining a corresponding sterilising chamber 252 crossed in the lower part thereof by the aforementioned conveyor 205, and is provided with a flow generating device 255 for generating an air flow F3 traversing and flowing into a bell 270, with a filtering element 260 or HEPA filter.

Accordingly, in the illustrated embodiment, the two modules 210 and 250 are arranged specularly so that the aforementioned intermediate passage 203 (FIG. 1) consists of corresponding openings made in the modules 210, 250 made to match each other.

Further openings made at the opposite ends of the modules 210, 250 respectively form the aforementioned loading inlet 201 and unloading outlet 202 of this sterilising unit 200.

As already mentioned above, both the first module 210 and the second module 250 may both operate as hot or cold sterilisers, as can now be seen in FIGS. 4 and 5.

According to what has been illustrated in the first of the above figures, FIG. 4, with which for simplicity and clarity it is intended for disclosing the first module 210 suitable for operating in hot-sterilising mode, in the first module 210 the sterilising chamber 212 is obtained, that is crossed in the lower part thereof by the aforementioned conveyor 205.

In the upper part of the first module 210 a path is made for an air flow F3 intended for being blown towards the bottles 2 in the manner disclosed below and comprising two heating and cooling branches 218 and 219 of the bottles 2 that are selectable alternately.

This path leads, above the conveyor 205, into the bell 230, below which the aforementioned filtering element 220 or HEPA filter is fixed.

Within the heating branch 218 a heating device 211 is located, substantially defined by a coil resistor intended for heating the aforementioned air flow to a preset sterilising/depyrogenating temperature of the bottles 2.

In the first module 210 the aforementioned generating device 215 of the aforementioned air flow is also provided.

The generating device 215 comprises an inlet fan 216, arranged at an air intake 213 and suitable for sucking in air from the external environment, and a main fan 217, arranged above the aforementioned bell 230 and suitable for conveying the air flow to the bottles 2 through the HEPA filter 220 in a substantially laminar mode.

The first sterilising module 210 furthermore comprises a refrigerating unit 225, that is selectively activatable and intended for rapidly cooling the air flow entering the aforementioned first module 210, when the latter is arranged in the cooling operating mode.

At the inlet of the aforementioned heating 218 and cooling 219 branches flow-switching members 221 are provided.

These substantially comprise a pair of butterfly switches 222, 223, that are switchable in push-pull mode between open and closed positions to connect or disconnect corresponding heating branches 218 and cooling branches 219 of the air flow F2 path.

In the upper part of the first module 210 an evacuation fan 224 is provided that is intended for conveying part of the circulating air flow to the external environment.

With this fan 224 a mixing valve 225*a* is associated that is arrangeable in different opening degrees intended for mixing in suitable proportions air coming from the external environment with the part of the air flow that enters the evacuation fan 224, to lower the temperature of the exiting air.

With reference now to FIG. 5, with which for simplicity and clarity it is intended for disclosing the second module 250 suitable for operating in cold mode, the second module 250 defines the sterilising chamber 252, crossed in the lower part thereof by the aforementioned conveyor 205.

In the upper part of the second module 250 a path for an air flow F3 is made comprising two heating 258 and cooling 259 branches. This path leads, above the conveyor 205, into the bell 270, below which the aforementioned HEPA filter 260 is fixed.

Inside the heating branch 258 a heating device 251 is arranged, that can be defined by a coil resistor and that is intended for heating the air flow to the aforementioned preset sterilising and depyrogenating temperature of the bottles 2.

In the second module 250 a generating device 255 above the aforementioned air flow F3 is also provided.

The generating device 255 comprises an inlet fan 256, arranged at an air intake 253 and suitable for sucking in air from the external environment, and a main fan 257, arranged above the aforementioned bell 270.

A refrigerating unit 265 is furthermore present that is selectively activatable and is intended for rapidly cooling the air flow F3 entering thereof the second module 210, when the latter is arranged in the cooling operating mode.

At the inlet of the aforementioned heating 258 and cooling 259 branches flow-switching members 261 are provided.

These substantially comprise a pair of butterfly switches 262, 263, that are switchable in push-pull mode as already disclosed previously.

In the upper part of the second module 250 an evacuation fan 264 is provided that is intended for conveying part of the flow of circulating air to the external environment.

With this fan 264 a corresponding mixing valve 265*a* is associated that is arrangeable for different degrees of opening to lower the temperature of the exiting air.

According to what is illustrated in FIG. 1, as already mentioned, between the aforementioned washing 100 and sterilising 200 stations a first conveyor 10 is provided, that can be of the known belt type and intended for removing bottles 2 from the outlet of the washing station 100, already washed and decontaminated, and for conveying the bottles 2 to the inlet 201 of the sterilising station 200.

Owing to the respective side-by-side arrangement of the aforementioned stations 100 and 200, the aforementioned first conveyor 10 is arranged transversely to the orientation of the system 1, thus defining part of the "U" portion of the aforementioned path A.

Still according to what is illustrated in FIG. 1, the system 1 furthermore comprises a filling and sealing station 300 for filling the bottles 2 with liquid substances and subsequent for sealing the bottles 2 with corresponding caps, the station 300 is arranged downstream of the aforementioned sterilising station 200 in relation to the path A; this filling and sealing station 300 is substantially aligned on the washing station 100 and is staggered in relation to the outlet line of the sterilising station 200, defining, together with a second transverse conveyor 20, a second "L"-shaped portion connected to the aforementioned "U"-shaped portion of the advancing path A of the bottles 2.

Such an arrangement enables a particularly compact system configuration to be obtained that makes it possible to contain the external dimensions within the limits set by the work plane of standard means of road transport, as shown above.

The filling and sealing station 300 is of the known type with linear development and overall comprises a filling unit 301 having a bank 302 of filling nozzles (known and not illustrated in FIG. 1), and a sealing cap-supplying and applying device 303 (not shown) arranged along a step-mode filling line defined between two conveyors 304 of the known star type and also provided with two successive weighing device for weighing bottles 2 and with a locking unit 306 of the bottles 2.

The filling station 300 can be structurally shaped in a manner similar to the Filling/Capping/Locking machine called "STERIFILL F200" designed and marketed by the same applicant.

The aforementioned filling and sealing station 300 is directly connected to the sterilising station 200 by the aforementioned second conveyor 20, of a type similar to the aforementioned first conveyor 10 and it is also transversely arranged.

The system 1 lastly comprises a sterile chamber 5 that extends above, by covering it, the portion of the system 1 situated downstream of the sterilising station 200, and namely the second conveyor 20 and the entire filling and sealing station 300.

In view of the particular arrangement thereof, the sterile chamber 5 therefore has an "L" shape with a first branch 5*a* arranged transversely and against the sterilising station 200 to enclose the second conveyor 20, and a second branch 5*b* arranged longitudinally at the outlet of the aforementioned filling and sealing station 300, and therefore of the outlet of the system 1.

The sterile chamber 5 is made with substantially known techniques by means of suitable isolating joint panels and is provided with suitable means for providing the regular sterilisation thereof, which is not shown for simplicity as it is completely known.

Substantially, the system 1 is assembled as a single and compact body, with sufficient structural rigidity to enable the packaging and conveying thereof without having to dismantle any part.

This aspect makes the managing of the system easier for the entire productive life thereof.

The system 1 can in fact be subjected to validation tests directly in the factory, as soon as assembled and then be directly packaged and conveyed to the production site.

As nothing of the component units thereof has been removed in the meantime, it is unnecessary to conduct new validation tests once in the packaging place.

It is in fact sufficient to conduct the switch-on of the so-called utilities (electric power supply, compressed air, supply line of the liquid product to be packaged etc.) by means of suitably placed inlets, then to conduct a normal operating test and conduct the necessary calibrating and synchronising operations in addition to an operation of first sterilisation of the sterile chamber 5.

The aforementioned procedure can also be applied whenever it is necessary to move the system 1 to another production site, for example in order to package a different product.

What has been set out above makes clear the great versatility of the this system and the simplicity with which the system can be set up to package different products, also on different operating sites.

All this makes the system particularly suitable both for packaging a single product in not particularly great quantities for a long period and for packaging batches of different products for short periods.

The configuration of the system therefore fully meets the needs of the modern pharmacological industry and in particular of the companies operating in the biotechnology field.

It is understood that everything disclosed above has been disclosed purely by way of non-limitative example. Possible modifications to and variations on the invention are therefore considered to fall within the extent of the protection accorded to this technical solution as disclosed above and claimed below.

The invention claimed is:

1. Compact system for packaging liquid products in a sterile environment, in particular pharmaceutical liquids injectable into suitable containers, the system comprising a plurality of operative packaging stations connected together and arranged in succession along an advancing path of said containers; said plurality of stations comprising at least a washing station intended for cleaning and decontaminating each of the said containers, at least a sterilising station for sterilising the containers exiting said washing station, and at least a filling and sealing station for filling said containers with said liquids and for sealing the containers; wherein said stations and a connecting arrangement thereof are mounted in an operating configuration on a sole work platform; said washing station and said sterilising station being arranged parallel to one another and placed alongside and connected together by a first conveyor of the containers arranged transversely to the washing station and the sterilising station to define a first substantially "U"-shaped portion of said path; said filling and sealing station being arranged aligned on said washing station and connected, in a staggered position, to said sterilising station by a second conveyor of said containers arranged transversely to the sterilising station to define a second substantially "L"-shaped portion of said advancing path; wherein said sterilising station comprises a two-stage sterilising/depyrogenating unit; said two-stage sterilising/depyrogenating unit being enclosed inside an insulated covering structure.

2. System according to claim 1, wherein said work platform defines a work area with an extent substantially the same as that of a loading plane of a standard road transport vehicle, so as to be compatible with loading and conveying of the entire system mounted on the loading plane.

3. System according to claim 1, wherein said washing station comprises a conveying plane for supporting and advancing in an orderly manner said containers to a grasping, moving and washing device; said grasping, moving and washing device comprises at least a conveyor provided with a grasping arrangement for grasping in succession groups of said containers from said conveying plane at a first operating position, and at least a bank of dispensing and diffusing nozzles for dispensing and diffusing liquid washing substances inside the containers; the station further comprising an actuating arrangement for moving with reciprocating motion to each other said conveyor and said bank of nozzles to cause the insertion of the nozzles inside groups of said containers at a second operating position.

4. System according to claim 3, wherein said conveyor comprises a belt that is movable in step mode around corresponding pulleys and is provided with grasping grippers for grasping the containers; grasping one of said groups of containers from said conveying plane by said grippers in the first operating position being achieved simultaneously and during said inserting of said nozzles inside containers of a successive group of containers into said second operating position.

5. System according to claim 1, wherein said sterilising/depyrogenating unit comprises at least two sterilising/depyrogenating modules which are actuatable independently of one another according to hot and/or cold sterilising modes of the containers.

6. System according to claim 5, wherein said two sterilising/depyrogenating modules are substantially identical to each other.

7. System according to claim 5, wherein each of said sterilising/depyrogenating modules comprises a heating device, suitable for heating an air flow intended for being blown towards said containers inside a sterilising chamber to take said containers to a preset sterilising and depyrogenating temperature; a generating device of said air flow suitable for generating and conveying the same flow to said containers along a heating path crossing said heating device; a filtering element suitable for filtering said air flow up to a preset degree of purity; flow-switching members arranged along said air flow and switchable to define said heating path.

8. System according to claim 7, wherein said flow-switching members comprise at least a pair of butterfly switches switchable in push-pull mode between the respective open/closed positions.

9. System according to claim 7, wherein each of said sterilising/depyrogenating modules comprises an evacuation fan suitable for conveying part of said air flow to the external environment; a corresponding mixing valve being associated with said evacuation fan.

10. System according to claim 5, wherein each of said sterilising/depyrogenating modules comprises a refrigerating device, suitable for refrigerating an air flow intended for being blown towards said containers inside a sterilising chamber to take said containers to a preset sterilising and depyrogenating temperature; a generating device of said air flow, suitable for generating and conveying the same flow to said containers along a cooling path crossing said refrigerating device; a filtering element suitable for filtering said air flow up to a preset degree of purity; flow-switching members arranged along said air flow and switchable to define said cooling path.

11. System according to claim 10, wherein said flow-switching members comprise at least a pair of butterfly switches switchable in push-pull mode between the respective open/closed positions.

12. System according to claim 10, wherein each of said sterilising/depyrogenating module comprises an evacuation fan suitable for conveying part of said air flow to the external environment; a corresponding mixing valve being associated with said evacuation fan.

13. Compact system for packaging liquid products in a sterile environment, in particular pharmaceutical liquids injectable into suitable containers, the system comprising a plurality of operative packaging stations connected together and arranged in succession along an advancing path of said containers; said plurality of stations comprising at least a washing station intended for cleaning and decontaminating each of the said containers, at least a sterilising station for sterilising the containers exiting said washing station, and at least a filling and sealing station for filling said containers with said liquids and for sealing the containers; wherein said stations and a connecting arrangement thereof are mounted in an operating configuration on a sole work platform; said washing station and said sterilising station being arranged parallel to one another and placed alongside and connected together by a first conveyor of the containers arranged transversely to the washing station and the sterilising station to define a first substantially "U"-shaped portion of said path; said filling and sealing station being arranged aligned on said washing station and connected, in a staggered position, to said sterilising station by a second conveyor of said containers arranged transversely to the sterilising station to define a second substantially "L" shaped portion of said advancing path; wherein the system further comprises a sterile chamber, that extends above, by covering it, the portion of the system arranged downstream of said sterilising station along said "L"-shaped portion of said advancing path, and that said portion comprises said second conveyor and said filling and sealing station.

14. Compact system for packaging liquid products in a sterile environment, in particular pharmaceutical liquids injectable into suitable containers, the system comprising a plurality of operative packaging stations connected together and arranged in succession along an advancing path of said containers; said plurality of stations comprising at least a washing station intended for cleaning and decontaminating each of the said containers, at least a sterilising station for sterilising the containers exiting said washing station, and at least a filling and sealing station for filling said containers with said liquids and for sealing the containers; wherein said stations and a connecting arrangement thereof are mounted in an operating configuration on a sole work platform; said washing station and said sterilising station being arranged parallel to one another and placed alongside and connected together by a first conveyor of the containers arranged transversely to the washing station and the sterilising station to define a first substantially "U"-shaped portion of said path; said filling and sealing station being arranged aligned on said washing station and connected, in a staggered position, to said sterilising station by a second conveyor of said containers arranged transversely to the sterilising station to define a second substantially "L" shaped portion of said advancing path; wherein said filling and sealing station substantially comprises at least a filling unit having at least a bank of filling nozzles, at least a supplying and applying device of closing caps arranged along a filling line defined between two star conveyors; the station also being provided with weighing devices for weighing said containers and with a locking unit for locking the containers.

15. Compact system for packaging liquid products in a sterile environment, in particular pharmaceutical liquids injectable into suitable containers, the system comprising a plurality of operative packaging stations connected together and arranged in succession along an advancing path of said containers; said plurality of stations comprising at least a washing station intended for cleaning and decontaminating each of the said containers, at least a sterilising station for sterilising the containers exiting said washing station, and at least a filling and sealing station for filling said containers with said liquids and for sealing the containers; wherein said stations and a connecting arrangement thereof are mounted in an operating configuration on a sole work platform; wherein said sterilising station comprises a two-stage sterilising/depyrogenating unit; said two-stage sterilising/depyrogenating unit being enclosed inside an insulated covering structure.

16. Compact system for packaging liquid products in a sterile environment, in particular pharmaceutical liquids injectable into suitable containers, the system comprising a plurality of operative packaging stations connected together and arranged in succession along an advancing path of said containers; said plurality of stations comprising at least a washing station intended for cleaning and decontaminating each of the said containers, at least a sterilising station for sterilising the containers exiting said washing station, and at least a filling and sealing station for filling said containers with said liquids and for sealing the containers; wherein said stations and a connecting arrangement thereof are mounted in an operating configuration on a sole work platform; said filling and sealing station being connected to said sterilising station by a conveyor of said containers arranged transversely to said sterilising station; the system further comprising a sterile chamber, that extends above, by covering it, a portion of said system arranged downstream of said sterilising station, said portion comprising said conveyor and said filling and sealing station.

17. Compact system for packaging liquid products in a sterile environment, in particular pharmaceutical liquids injectable into suitable containers, the system comprising a plurality of operative packaging stations connected together and arranged in succession along an advancing path of said containers; said plurality of stations comprising at least a washing station intended for cleaning and decontaminating each of the said containers, at least a sterilising station for sterilising the containers exiting said washing station, and at least a filling and sealing station for filling said containers with said liquids and for sealing the containers; wherein said stations and a connecting arrangement thereof are mounted in an operating configuration on a sole work platform; said filling and sealing station substantially comprising at least a filling unit having at least a bank of filling nozzles, at least a supplying and applying device of closing caps arranged along a filling line defined between two star conveyors; the station also being provided with weighing devices for weighing said containers and with a locking unit for locking the containers.

* * * * *

UNITED STATES PATENT AND TRADEMARK OFFICE

CERTIFICATE OF CORRECTION

PATENT NO. : 7,581,367 B2
APPLICATION NO. : 11/795133
DATED : September 1, 2009
INVENTOR(S) : Bechini It is certified that error appears in the above-identified patent and that said Letters Patent is hereby corrected as shown below:

On the Title Page

Delete Item "(73) Assignee: I.M.A. Industria Macchine Automatiche S.p.A." and insert Item --(73) Assignee: IMA LIFE S.R.L.--.

Signed and Sealed this
Fourteenth Day of February, 2012

David J. Kappos
*Director of the United States Patent and Trademark Office*